US00PP11800P2

(12) United States Plant Patent
Bautista

(10) Patent No.: US PP11,800 P2
(45) Date of Patent: Mar. 13, 2001

(54) HELICHRYSUM PLANT NAMED 'HARVEST SUN II'

(75) Inventor: Rodolfo Valdoz Bautista, Half Moon Bay, CA (US)

(73) Assignee: Bay City Flower Company, Inc., Half Moon Bay, CA (US)

( * ) Notice: Under 35 U.S.C. 154(b), the term of this patent shall be extended for 0 days.

(21) Appl. No.: 09/150,641

(22) Filed: Aug. 26, 1998

(51) Int. Cl.[7] ..... A01H 5/00
(52) U.S. Cl. ..... Plt./359
(58) Field of Search ..... Plt./359

(56) References Cited

U.S. PATENT DOCUMENTS

| | | | |
|---|---|---|---|
| P.P. 9,660 | 10/1996 | Bautista | Plt./359 |
| P.P. 9,661 | 10/1996 | Bautista | Plt./359 |
| P.P. 9,666 | 10/1996 | Bautista | Plt./359 |
| P.P. 9,667 | 10/1996 | Bautista | Plt./359 |
| P.P. 10,193 | 1/1998 | Elliot et al. | Plt./359 |
| P.P. 10,742 | 12/1998 | Bautista | Plt./359 |
| P.P. 10,834 | 3/1999 | Bautista | Plt./359 |

OTHER PUBLICATIONS

Liberty Hyde Bailey & Ethel Zoe Bailey, Hortus Third—A Concise Dictionary of Plants . . . , Macmillan Publishing Company, New York, 1976.

Huxley, A., Griffiths, M., Levy, M. Helichrysum. The New Royal Horticultural Society Dictionary of Gardening. Stockton Press. pp. 525–529, 1992.*

* cited by examiner

*Primary Examiner*—Bruce R. Cambell
*Assistant Examiner*—Michelle Kizilkaya
(74) *Attorney, Agent, or Firm*—James R. Cypher; Charles R. Cypher

(57) ABSTRACT

The present invention relates to a new and distinct variety of the Compositae family, named *Helichrysum bracteatum*× *splendidum* 'Harvest Sun II', which originated as a seedling from the inventor's controlled crossing of unnamed and unpatented individuals *Helichrysum bracteatum* (Venten.) Andr. with *Helichrysum splendidum* (Thunb.) Less. The characteristics of the new variety which in combination distinguish it from its patents and all other varieties known to the inventor are: the color of its flower head and bud, its resistance to the root disease Pythium, its puberulent and sparsely villous leaves, its compact growth habit, its ability to grow well in pots in which it can be sold, and the ease with which it can be forced to flower outside for sale in the autumn without growth regulators. Coloring of bracts on the upperside of the flower head gives the mature flower head a uniform appearance of R.H.S. 12A (yellow group) at maturity.

4 Drawing Sheets

BACKGROUND OF THE INVENTION

The present invention relates to a new and distinct variety of the Compositae family. The new variety is named *Helichrysum bracteatum*×*splendidum* 'Harvest Sun II' by the assignee, Bay City Flower Company, Inc. The inventor is Rodolfo Valdoz Bautista of Half Moon Bay, Calif., a citizen of the Philippines.

This new Helichrysum variety originated as a seedling. It was selected from the progeny of a controlled hybridization conducted by the inventor in a commercial nursery in the city of Half Moon Bay. Half Moon Bay is located in San Mateo County, in the state of California.

The inventor crossed *Helichrysum splendidum* (Thunb.) Less. and *Helichrysum bracteatum* (Venten.) Andr. to produce the new variety. The parent plants were unnamed, proprietary cultivars. Neither of the parents are patented. The new variety was selected for commercial development because of its unique flower head color and compact growth habit. The new variety is particularly suitable for commercial plant culture because of its long-lasting flowers and attractive coloring.

The characteristics of the new variety which in combination distinguish it from its parents and all other varieties known to the inventor are: the color of its flower head and bud, its resistance to the root disease Pythium, its puberulent and sparsely villous leaves, its compact growth habit, its ability to grow well in pots in which it can be sold, and the ease with which it can be forced to flower outside for sale in the autumn without growth regulators.

The coloring of the flower head of the new variety changes as the flower head opens revealing more bracts. The bud stage is darkest. The outermost involucral bracts of the bud are R.H.S. 167B (greyed-orange group) at their tips. As the bud opens, a first group of inner bracts become visible. This group of bracts has tip and rib portions that are R.H.S. 167B (greyed-orange group) but are otherwise colored R.H.S. 9A (yellow group). Buds that are just beginning to open have an overall appearance of R.H.S. 26A (orange group). As the flower head matures, the tips and middle portions of the outermost bracts become R.H.S. 167A (greyed-orange group). These bracts are visible on the underside of a fully-mature flower head. The middle bracts have tips that are R.H.S. 167B (greyed-orange group), but are otherwise predominantly R.H.S. 12A (yellow group). These bracts are visible on the upper side of the mature flower head. The innermost bracts are mostly one color: R.H.S. 12A (yellow group). Coloring of bracts on the upperside of the flower head gives the flower head a uniform appearance of R.H.S. 12A (yellow group) at maturity.

The new variety, when planted in the summer for sale in the autumn season, can be forced to salable product in 11 to 13 weeks under prevailing daylengths and outdoor conditions in Half Moon Bay, Calif.

The following table compares the new variety to the closest varieties known to the inventor, according to the new variety's distinguishing characteristics. The variety designated '1A93' is also a progeny of a cross between the unnamed, proprietary parent cultivars: *Helichrysum splendidum* (Thunb.) Less. and *Helichrysum bracteatum* (Venten.) Andr. The variety designated 'Harvest Sun' is the progeny of a cross between the variety designated '1A93' and the parent plant of the new variety, *Helichrysum bracteatum* (Vent.). Andr. The individual designated '1A93' is a unnamed, propreitary cultivar that is not patented. The cultivar identified as 'Harvest Sun' is the subject of U.S. Plant Pat. No. 9,660.

| | *H. bracteatum* (general characteristics) | *H. splendidum* (parent) | '1A93' | 'Harvest Sun' USPP 9,660 | New Variety |
|---|---|---|---|---|---|
| Bract color | Various colors | Involucral bracts at opening are predominantly R.H.S. 12A. Upper involucral bracts when flower head is mature are predominantly R.H.S. 12A. | R.H.S. 4A | Involucral bracts at opening are predominantly R.H.S. 22A. Upper involucral bracts when flower head is mature are predominantly R.H.S. 9A. | Involucral bracts at opening are predominantly R.H.S. 12A. Upper involucral bracts when flower head is mature are predominantly R.H.S. 12A. |
| Bud color | Various colors | Predominantly R.H.S. 175A. | R.H.S. 187B | R.H.S. 26A | Predominantly R.H.S. 26A. |
| Disease resistance | Not resistant to Pythium | Resistant to Pythium | Resistant to Pythium | Resistant to Pythium | Resistant to Pythium |
| leaf surfaces | puberulent | tomentose | puberulent and sparsely villous, main veins are hirsute | puberulent and sparsely villous, main veins are hirsute | puberulent and sparsely villous, main veins are hirsute |
| Suitability for pot culture | Good | Average | Good | Good | Good |
| Ease of forcing | Generally good | Difficult | Good | Good | Good |
| Growth habit | Generally compact | Spreading | Compact | Compact | Compact |
| Flowering habit | Long-lasting | Long-lasting | 7 weeks | 7 weeks | 7 weeks |

The distinguishing characteristics are retained by asexually reproduced, successive generations. The inventor, at a commercial nursery in Half Moon Bay, Calif., has asexually reproduced the new variety through three successive generations by means of cuttings and has found that the combination of characteristics as herein disclosed remain firmly fixed.

BRIEF DESCRIPTION OF THE DRAWINGS

The accompanying drawings consist of color photographs that show the typical potted-plant form, including the inflorescence, foliage, and bract color development from the bud stage to the mature flower head. The colors are represented as truly as possible using conventional photographic procedures.

FIG. 1 is a perspective view of a potted plant of the new variety described herein, illustrating the overall form and appearance of the plant in full bloom.

FIG. 2 is a top view of a potted plant of the new variety described herein, illustrating the overall form and appearance of the plant in full bloom.

DETAILED DESCRIPTION OF THE NEW VARIETY

Figure 3:
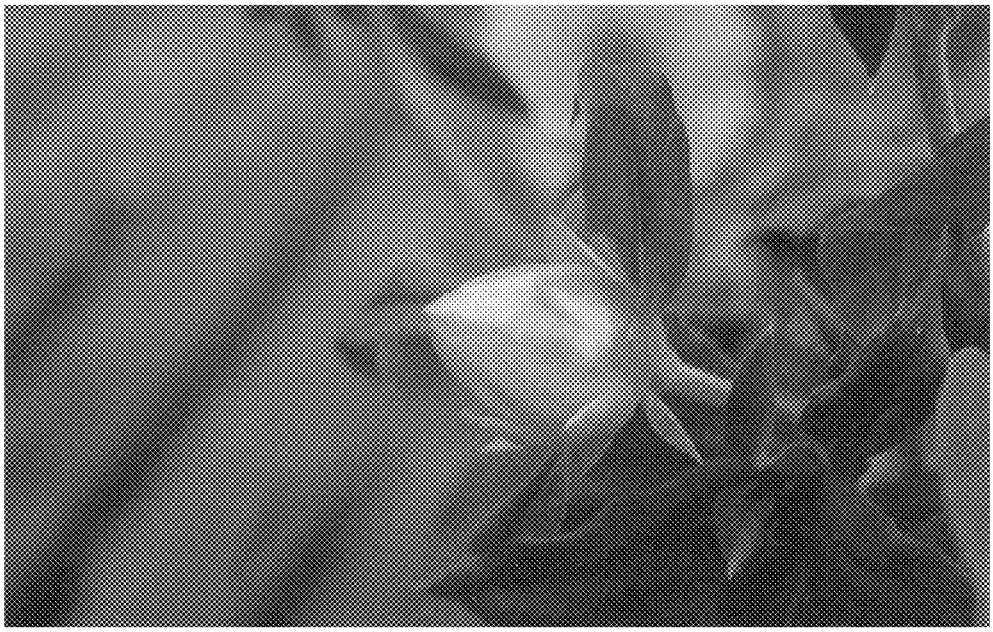
FIG. 3 is a view of a bud of the new variety described herein.
Figure 4:
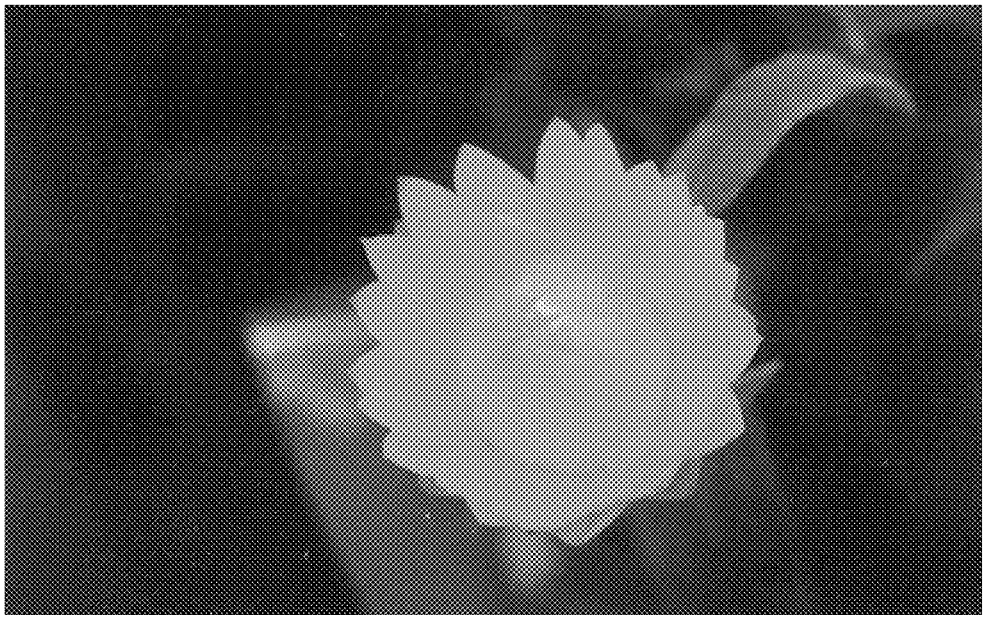
FIG. 4 is a view of a bud which is beginning to open, showing the overall appearance of the flower head at this stage.
Figure 5:
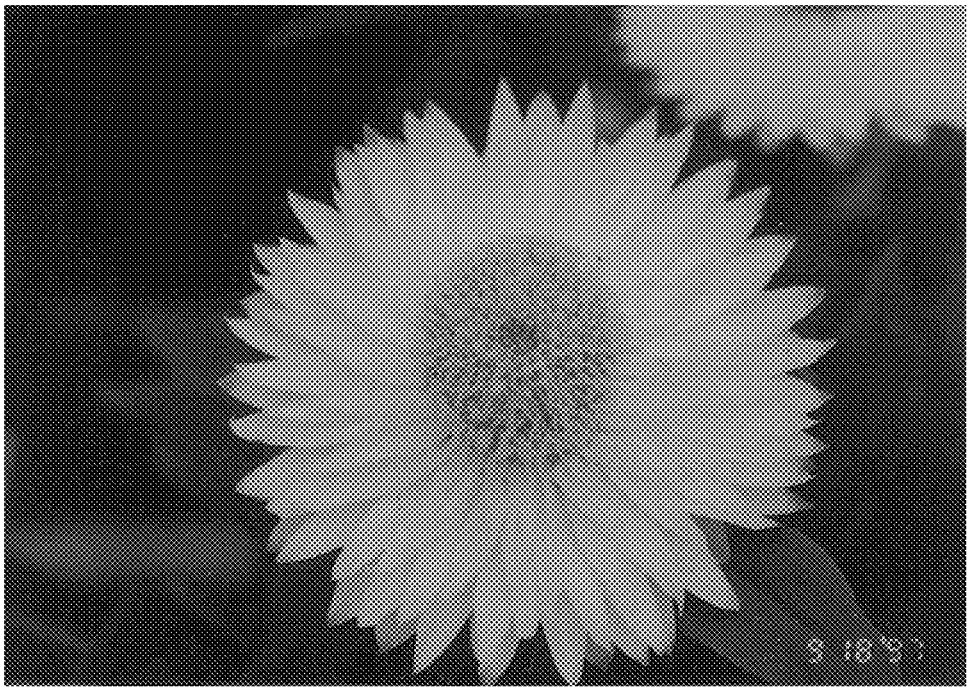
FIG. 5 is a top view of a mature flower head of the new variety described herein, showing the pigmentation pattern of the bracts.
Figure 6:
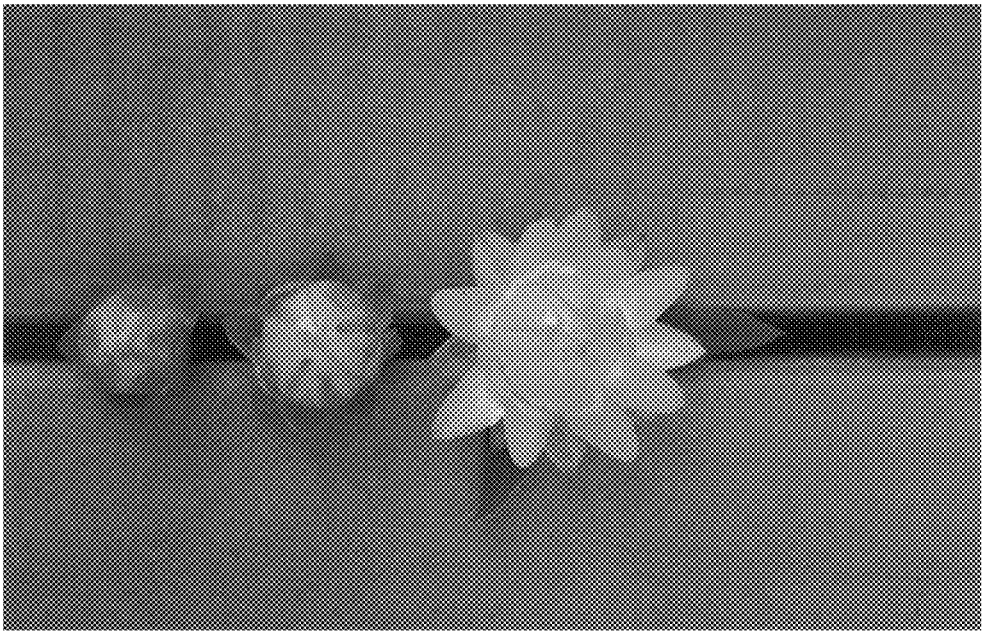
FIG. 6 is a top view of three buds in differing stages of opening.
Figure 7:
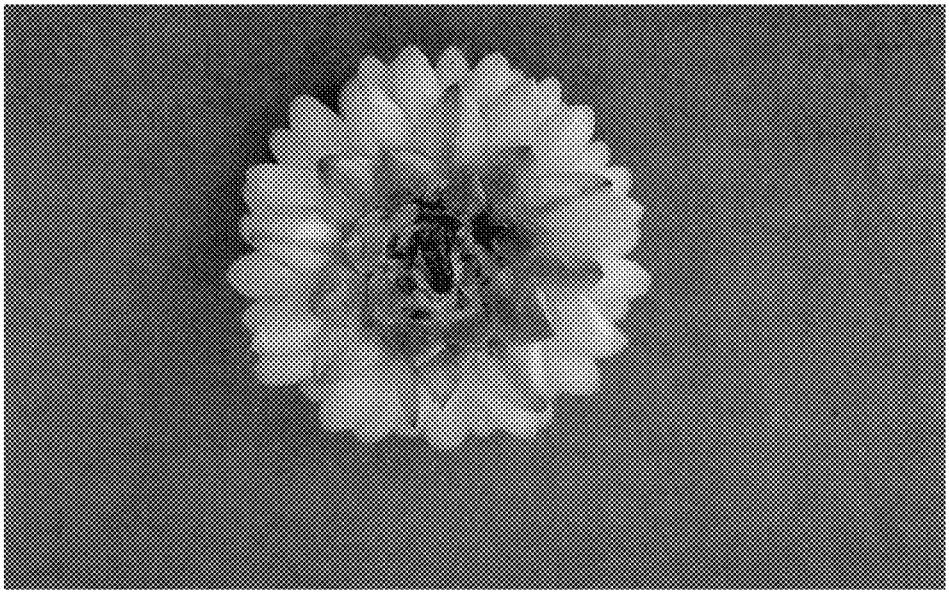
FIG. 7 is a view of the underside of an individual flower head of the new variety described herein, showing the pigmentation pattern of the bracts.
Figure 8:
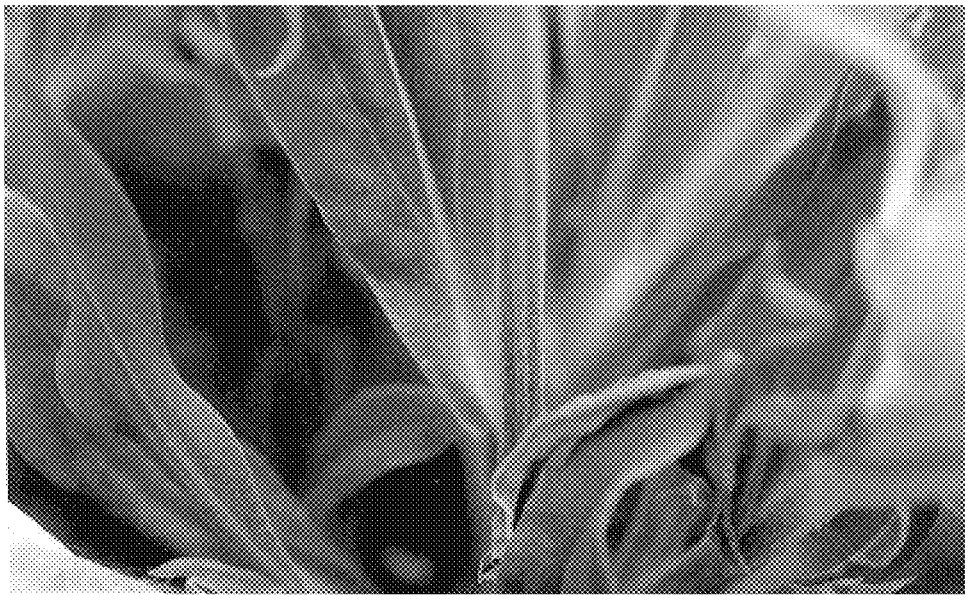
FIG. 8 is side view of a stem of a new variety.

The following is a detailed description of the new variety. The new variety has not been observed under all possible environmental conditions. Color designation and other values stated may deviate slightly from the stated values from flowering to flowering, but the deviations will be within the range expected from varying environmental, seasonal and cultural conditions. Color designations were made according to The R.H.S. Color Chart published by The Royal Horticultural Society of London, England.

The following description is based on observations of optimally fertilized plants grown outside in 11 cm pots. Cuttings were taken from mature plants in the summer and placed in 4×6 cm cell trays. Roots began visible initiation after approximately 2 weeks. Plants were transplanted to 11 cm pots approximately 4 to 6 weeks after sticking, and moved out of the greenhouse. Plants were pinched 3 to 4 weeks after transplanting. A growth regulator was applied approximately 3 weeks after pinching. The growth regulator used goes by the trade name Bonzi. It is made by Union Chemical. The active ingredient is Paclobutrazol (±)-(R*, R*)-b–((4-Chlorophenyl)methyl)-a-(1,1, -dimethlylethyl)-1H-1,2,4, -triazole- 1-ethanol. It is the subject of U.S. Pat. No. 4,243,405. Bonzi is 0.4% active ingredient. The Bonzi formulation was diluted by mixing 2 ounces per gallon, and then applied to the plants by drenching them.

The observed plants were 13 weeks old. The plants were grown under the prevailing daylengths and temperatures in Half Moon Bay, Calif., during the summer and autumn months. In Half Moon Bay, the average temperature during the day is 60 degrees Fahrenheit. The average temperature during the night is 51 degrees Fahrenheit.

THE PLANT

Name: *Helichrysum bracteatum×splendidum* 'Harvest Sun II'.
Origin: Seedling.
Parentage:
*Seed parent.*—*Helichrysum splendidum* (Thunb.) Less.
*Pollen parent.*—*Helichrysum bracteatum* (Venten.) Andr.
Classification:
*Family.*—Compositae.
*Tribe.*—Inula.
*Genus.*—Helichrysum.
*Species.*—*Helichrysum bracteatum×splendidum.*
*Commercial.*—Strawflower.
Form: Upright, compact, perennial herb.
Height: Plant grown in 11 cm pot is 21.5 cm.
Diameter: Plant grown in 11 cm pot is 33 cm.
Circumference: Plant grown in 11 cm pot is 81 cm.
Growth: Upright, vigorous growth outdoors with excellent branching; easily forced to bloom without growth regulators.
Stems:
*Texture.*—Generally, stems are moderately pubescent; stems are very pubescent below the flower, hairs lessen further down the stem. Stems are sericeous giving a glaucous appearance.
*Size.*—Stem width at top of plant is 5 mm. Stem width at base of plant is 6 mm. Stem width at widest point is 6 mm.
Foliage:
*Quantity.*—Abundant.
*Shape.*—Linear; narrowly acute; margins are entire to repand.
*Size.*—As large as 17 cm long by 3.5 cm wide.
*Texture.*—Viscid; main vein dominates on the underside of leaf and is sunken on the leaf surface.
*Pubescence.*—Leaf surfaces are puberulent, and sparsely villous; main veins are hirsute.
*Color.*—Upper leaf surface is R.H.S. 137A (green group); lower leaf surface is R.H.S. 137C (green group).
*Petiole.*—Nonexistent.
*Leaf attachment.*—Semi-amplexicaul.
Disease resistance: Resistant to the root disease Pythium.

The Bud

Form: Conical, with imbricate involucral bracts.
Texture: Smooth and glossy (waxy).
Rate of opening: Slowly, and in layers, closing at night; fully open 2–3 weeks.
Size:
*Diameter.*—2.0 cm.
*Circumference.*—5.0 cm.
Involucral bracts:
*Color.*—Outermost involucral bracts are R.H.S. 167B (greyed-orange group) at their tips. As bud opens, a first group of inner bracts become visible. This group of bracts has tip and rib portions that are R.H.S. 167B (greyed-orange group) but are otherwise colored R.H.S. 9A (yellow group). Buds that are just beginning to open have an overall appearance of R.H.S. 26A (orange group).
*Aspect.*—Thin, dry, membranous.

The Inflorescence

Form: Flower head is discoid and solitary; usually 1 or 2 buds at the next leaf axis below.
Flower head size:
*Diameter.*—6.0 cm.
*Circumference.*—20 cm.
Disc floret portion diameter: 2.4–2.5 cm.
Shape of the flower head: Circular; involucral bracts are numerous and imbricate.
Appearance of the flower head: Showy.
Involucral bracts:
*Form.*—Involucral bracts are imbricate in many rows. Involucral bracts are scarious and membranous, but are brightly colored. The involucral bracts are deltoid, enlarged and petal-like.
*Color.*—Outermost bracts are R.H.S. 167A (greyed-orange group) at their tips and middle portions. These bracts are visible on the underside of a fully matured flower head. The middle bracts have tips that are R.H.S. 167B (greyed-orange group), but are otherwise predominatly R.H.S. 12A (yellow group). These bracts are visible on the upper side of the mature flower head. The innermost bracts are mostly one color: R.H.S. 12A (yellow group). Coloring of bracts on the upperside of the flower gives the flower a uniform appearance of R.H.S. 12A (yellow group) at maturity.
Disc florets:
*Form.*—Florets are all small, bisexual and tubular. The corolla of the florets is usually 5-lobed. Corolla is usually 11 mm long and glaucous (waxy). The upper 3.5 mm of the corolla is usually brightly colored.
*Androecium.*—There are usually 5 stamens borne on the corolla tube. The stamens, including the anthers, are ususally united into a tube around the style and become highly reflexed from the point of separation. The stamens protrude from the corolla. Pollen occurs on the adaxial surface of the anthers.
*Gynoecium.*—One pistil per disc floret. The ovary is inferior. The style is often branched. The style protrudes from the corolla. The stigma is bright yellow.
*Color.*—The colored upper portion of the corolla is also bright yellow.
Pollen color: R.H.S. 23A (yellow-orange group).
Blooming habit: The new variety, when planted in the summer for sale in the autumn season, can be forced to salable product in 11 to 13 weeks under prevailing daylengths and outdoor conditions in Half Moon Bay, Calif. The terminal inflorescence persists approximately 7 weeks on the plant. Usually, lateral inflorescence are present and begin blooming as the terminal inflorescence dies. If old inflorescence are removed, new inflorescence will continue to appear and bloom. New buds are produced on new growth all year long, if growing conditions allow, such as under the prevailing daylengths and temperatures at Half Moon Bay, Calif.
Persistence: 7 weeks.
Fragrance: None.
Achenes: Flowers produce nearly cylindrical or 5-angled achenes that are approximately 3 mm in length and 1 mm wide. The achenes have a pappus of bristles. The bristles are plumose at their apex. The achenes are dry and hard. The achenes rarely germinate.

Suitability as cut flower: The new plant last 10 to 14 days as a cut flower. After 10 to 14 the days, the flower head still substantially retains its shape and color, but the stems and foliage generally begain to rot.

I claim:

1. A new and distinct variety of Helichrysum plant, as illustrated and described.

* * * * *

FIGURE 1
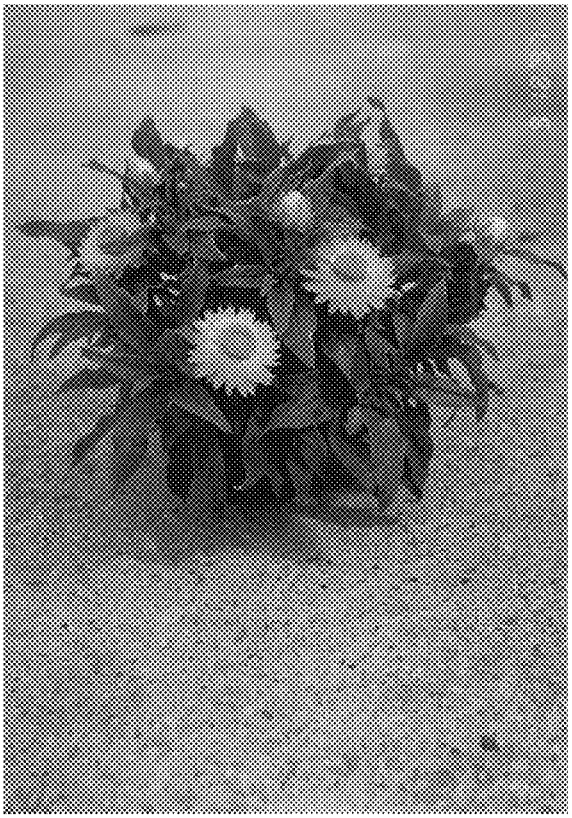
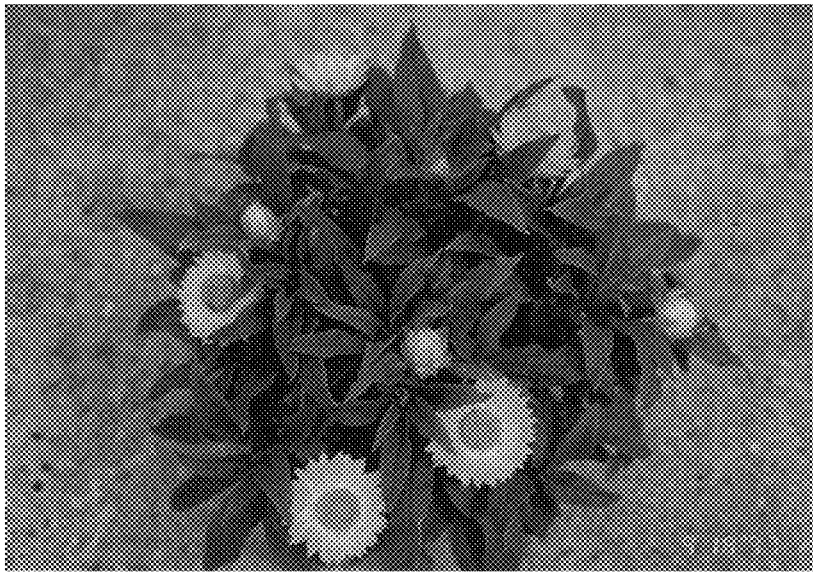
FIGURE 2